(12) United States Patent
Suganuma et al.

(10) Patent No.: US 11,578,158 B2
(45) Date of Patent: *Feb. 14, 2023

(54) MATERIAL FOR INTRAOCULAR LENS

(71) Applicant: MENICON CO., LTD., Aichi (JP)

(72) Inventors: Yuya Suganuma, Aichi (JP); Hiroko Nomura, Aichi (JP); Tatsuya Ojio, Aichi (JP); Keishi Tsukamoto, Aichi (JP)

(73) Assignee: MENICON CO., LTD., Aichi (JP)

( * ) Notice: Subject to any disclaimer, the term of this patent is extended or adjusted under 35 U.S.C. 154(b) by 138 days.

This patent is subject to a terminal disclaimer.

(21) Appl. No.: 16/960,098

(22) PCT Filed: Jan. 31, 2018

(86) PCT No.: PCT/JP2018/003227
§ 371 (c)(1),
(2) Date: Jul. 6, 2020

(87) PCT Pub. No.: WO2019/150490
PCT Pub. Date: Aug. 8, 2019

(65) Prior Publication Data
US 2021/0061933 A1    Mar. 4, 2021

(51) Int. Cl.
*C08F 220/12* (2006.01)
*C08F 220/30* (2006.01)
(Continued)

(52) U.S. Cl.
CPC ............ *C08F 220/12* (2013.01); *A61L 27/16* (2013.01); *C08F 220/281* (2020.02);
(Continued)

(58) Field of Classification Search
CPC .......... C08F 220/1806; C08F 220/1807; C08F 220/12; C08F 220/16; C08F 220/281;
(Continued)

(56) References Cited

U.S. PATENT DOCUMENTS 5,416,132 A * 5/1995 Yokoyama ............. G02B 1/043
526/279
6,140,438 A   10/2000 Ojio et al.
(Continued)

FOREIGN PATENT DOCUMENTS

AU   2017303210   1/2019
CN   103946251    7/2014
(Continued)

OTHER PUBLICATIONS

"Office Action of Australia Counterpart Application", dated Feb. 10, 2021, p. 1-p. 9.

(Continued)

*Primary Examiner* — Ling Siu Choi
*Assistant Examiner* — David L Miller
(74) *Attorney, Agent, or Firm* — JCIPRNET

(57) ABSTRACT

The present invention provides a material for intraocular lens which has improved hydrolysis resistance. The material for intraocular lens according to the present invention is obtained by polymerizing a monomer composition comprising: a base monomer, a hydrophilic monomer, and a crosslikable monomer, wherein the base monomer comprises an aromatic ring-containing acrylate monomer and an alkoxyalkyl methacrylate monomer having an alkoxyalkyl group having four or less carbon atoms. A blending ratio on a molar basis of the methacrylate monomer with respect to the acrylate monomer in all the monomer components contained in the monomer composition is 0.25 to 1.00.

5 Claims, 1 Drawing Sheet

(51) Int. Cl.
*A61L 27/16* (2006.01)
*C08F 220/28* (2006.01)
*C08F 220/16* (2006.01)
*C08F 220/18* (2006.01)

(52) U.S. Cl.
CPC ........ *C08F 220/30* (2013.01); *C08F 220/301* (2020.02); *A61L 2430/16* (2013.01); *C08F 220/16* (2013.01); *C08F 220/1806* (2020.02); *C08F 220/1807* (2020.02)

(58) Field of Classification Search
CPC ............... C08F 220/30; C08F 220/301; C08F 220/302; C08F 220/303; C08F 220/305; C08F 220/306; C08F 220/307; C08F 220/308; A61L 27/26; A61L 4230/16
See application file for complete search history.

(56) References Cited

U.S. PATENT DOCUMENTS

| | | | |
|---|---|---|---|
| 10,716,875 | B2 * | 7/2020 | Suganuma ............... A61L 27/16 |
| 2002/0027302 | A1 | 3/2002 | Benz et al. |
| 2013/0109779 | A1 * | 5/2013 | Argal .................... A61F 2/1613 523/113 |
| 2013/0253159 | A1 | 9/2013 | Benz et al. |
| 2018/0021475 | A1 | 1/2018 | Nomura et al. |

FOREIGN PATENT DOCUMENTS

| | | |
|---|---|---|
| CN | 104284942 | 1/2015 |
| CN | 106632926 | 5/2017 |
| EA | 018219 | 6/2013 |
| EP | 0898972 | 3/1999 |
| EP | 3251703 | 12/2017 |
| JP | H1156998 | 3/1999 |
| JP | 2003144538 | 5/2003 |
| JP | 2009045329 | 3/2009 |
| JP | 2015502763 | 1/2015 |
| WO | 2006113290 | 10/2006 |
| WO | 2009025399 | 2/2009 |
| WO | 2012004744 | 1/2012 |
| WO | 2012004746 | 1/2012 |
| WO | 2016121804 | 8/2016 |

OTHER PUBLICATIONS

"Office Action of Russia Counterpart Application", dated Feb. 20, 2021, p. 1-p. 19.
"Office Action of China Counterpart Application", dated Sep. 14, 2021, with English translation thereof, p. 1-p. 15.
"Office Action of Canada Counterpart Application," dated Aug. 26, 2021, p. 1-p. 6.
"Search Report of Europe Counterpart Application", dated Aug. 9, 2021, p. 1-p. 7.
"Office Action of Kazakhstan Counterpart Application", dated Aug. 18, 2021, with English translation thereof, p. 1-p. 6.
"Office Action of Russia Counterpart Application", dated Jul. 15, 2021, p. 1-p. 8.
Applicant's Comments and Response to 2nd Office Action in Patent Application in Russian Federation No. 2020124081, dated Jul. 15, 2021, p. 1-p. 4.
"International Search Report (Form PCT/ISA/210) of PCT/JP2018/003227," dated Mar. 6, 2018, with English translation thereof, pp. 1-2.
"Office Action of China Counterpart Application" with English translation thereof, dated Feb. 8, 2022, p. 1-p. 9.
"Office Action of Korea Counterpart Application" with English translation thereof, dated Mar. 17, 2022, p. 1-p. 12.
"Office Action of Japan Counterpart Application", dated Jun. 20, 2018, with English translation thereof, p. 1-p. 8.
"Office Action of Japan Counterpart Application", dated Oct. 10, 2018, with English translation thereof, p. 1-p. 5.
"Office Action of India Counterpart Application", dated Nov. 23, 2020, with English translation thereof, p. 1-p. 5.
"Office Action of Philippines Counterpart Application", dated Oct. 6, 2022, pp. 1-4.
"Office Action of Uzbekistan Counterpart Application", dated Aug. 3, 2022, with English translation thereof, pp. 1-4.
"Office Action of Brazil Counterpart Application", dated Apr. 26, 2022, with English translation thereof, pp. 1-8.
Office Action of Malaysia Counterpart Application, dated Aug. 18, 2022, pp. 1-3.

* cited by examiner

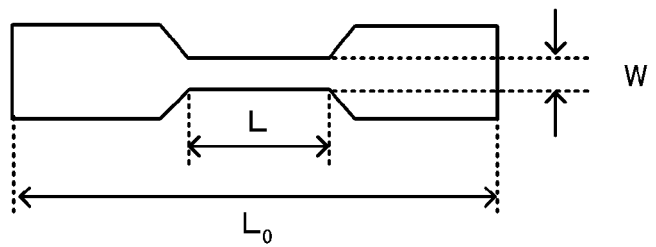

MATERIAL FOR INTRAOCULAR LENS

CROSS-REFERENCE TO RELATED APPLICATION

This application is a 371 of international application of PCT application serial no. PCT/JP2018/003227, filed on Jan. 31, 2018. The entirety of the above-mentioned patent application is hereby incorporated by reference herein and made a part of this specification.

BACKGROUND OF THE INVENTION

Technical Field

The present invention relates to a material for intraocular lens.

Related Art

An intraocular lens is a lens that is inserted into the eye instead of a crystalline lens during cataract surgery. Flexible and foldable materials have been developed in order that the material can be inserted into the eye from the possible smallest incision.

Because of excellent flexibility and high refractive index, acrylic materials have become the mainstream in recent years.

For example, in patent literature 1, a material for intraocular lens is proposed which is made of a polymer obtained by polymerizing a polymerization component containing hydrophilic monomers including hydroxyl group-containing alkyl (meth)acrylate, (meth)acrylamide monomer, N-vinyllactam and the like, and which has a water absorption of 1.5 to 4.5 mass %. Because the material for intraocular lens is excellent in flexibility and has a high refractive index, the lens can be made thinner and can be inserted from an incision in a folded state. Furthermore, glistening is suppressed and the lens may have excellent transparency.

LITERATURE OF RELATED ART

Patent Literature

Patent literature 1: Japanese Patent Laid-Open No. 11-56998

SUMMARY

Problems to be Solved

The acrylic material for intraocular lens may be hydrolyzed in an aqueous solution, and the hydrolyzate may be eluted in the eye, although the amount is small. The present invention is completed in view of the problem, and therefore, a main objective of the present invention is to provide a material for intraocular lens having improved hydrolysis resistance.

Means to Solve Problems

The inventors have studied the above problem and found that a material of intraocular lens, in which occurrence of glistening is suppressed and hydrolysis resistance is improved, is obtained by blending a specific alkoxyalkyl methacrylate monomer into a monomer composition comprising an aromatic ring-containing acrylate monomer, a hydrophilic monomer and a cross-likable monomer. On the other hand, it is clarified that the use of the alkoxyalkyl methacrylate monomer reduces the flexibility of the polymer material and may cause a problem in folding. Therefore, as a result of further studies by the inventors, it has been found that, by setting a blending ratio of the acrylate monomer and the methacrylate monomer in the monomer composition to a predetermined range, a polymer material is obtained in which flexibility suitable for folding is maintained and hydrolysis resistance is improved.

That is, a material of intraocular lens of the present invention is obtained by polymerizing a monomer composition comprising: a base monomer, a hydrophilic monomer, and a cross-likable monomer, wherein the base monomer comprises an aromatic ring-containing acrylate monomer and an alkoxyalkyl methacrylate monomer having an alkoxyalkyl group having four or less carbon atoms, and a blending ratio on a molar basis of the methacrylate monomer with respect to the acrylate monomer in all the monomer components contained in the monomer composition is 0.25 to 1.00.

In one embodiment, the alkoxyalkyl methacrylate monomer is one or more selected from methoxyethyl methacrylate and ethoxyethyl methacrylate.

In one embodiment, a blending amount of the alkoxyalkyl methacrylate monomer in the monomer composition is 1 mol % to 30 mol % when an amount of all the monomer components contained in the monomer composition is set as 100 mol %.

In one embodiment, a blending amount of the hydrophilic monomer in the monomer composition is 10 mol % to 40 mol % when the amount of all the monomer components contained in the monomer composition is set as 100 mol %.

In one embodiment, a blending amount of the cross-likable monomer in the monomer composition is 0.1 mol % to 5 mol % when the amount of all the monomer components contained in the monomer composition is set as 100 mol %.

In one embodiment, the aromatic ring-containing acrylate monomer has a phenoxy group, an alkylene group having two or less carbon atoms, and an acrylate bonding site.

In one embodiment, the monomer composition further comprises an alkyl acrylate monomer having an alkyl group having 1 to 20 carbon atoms.

In one embodiment, a blending amount of the alkyl acrylate monomer in the monomer composition is 15 mol % to 45 mol % when the amount of all the monomer components contained in the monomer composition is set as 100 mol %.

In one embodiment, the breaking stress of the material of intraocular lens is 4.5 MPa to 11.0 MPa.

Effect

According to the present invention, the material for intraocular lens is obtained in which flexibility suitable for folding is maintained and hydrolysis resistance is improved.

BRIEF DESCRIPTION OF THE DRAWINGS

FIG. 1 is an illustration diagram of a test piece used for breaking stress measurement.

DESCRIPTION OF THE EMBODIMENTS

Preferred embodiments of the present invention are described below, but the present invention is not limited to these embodiments.

In one embodiment, a material for intraocular lens of the present invention is obtained by polymerizing a monomer composition comprising: a base monomer, a hydrophilic monomer, and a cross-likable monomer, wherein the base monomer comprises an aromatic ring-containing acrylate monomer and an alkoxyalkyl methacrylate monomer having an alkoxyalkyl group having four or less carbon atoms. Preferably, the monomer composition further comprises, as a base monomer, an alkyl acrylate monomer having an alkyl group having 1 to 20 carbon atoms. In other words, the material for intraocular lens of the present invention contains repeating units derived from the above monomers.

The material of intraocular lens is characterized in that flexibility suitable for folding is maintained and hydrolysis resistance is excellent. The reason for this effect is not clear and is presumed as follows. That is, it is presumed that because a methacrylate structure is less susceptible to water attack than an acrylate structure due to the presence of a methyl group, the hydrolysis resistance of the obtained material can be improved by blending the methacrylate monomer with the base monomer. On the other hand, the flexibility of the material may be reduced by blending the methacrylate monomer with the base monomer, and flexibility (folding performance) desired for a material of intraocular lens can be exhibited by using a methacrylate monomer having an alkoxyalkyl group having four or less carbon atoms as the methacrylate monomer and by adjusting a blending ratio of the acrylate monomer and the methacrylate monomer in the monomer composition to a specific range. The material of intraocular lens may also have suppressed glistening, a high refractive index, and/or an excellent balance between flexibility and strength.

A. Monomer Composition

A-1. Base Monomer

The base monomer comprises an aromatic ring-containing acrylate monomer and an alkoxyalkyl methacrylate monomer having an alkoxyalkyl group having four or less carbon atoms. Depending on the objective, the base monomer may further comprise an alkyl acrylate monomer having an alkyl group having 1 to 20 carbon atoms. In the specification, the base monomer refers to a monomer constituting a main structure of the material for intraocular lens.

When an amount of all the monomer components contained in the monomer composition is set as 100 mol %, a blending amount of the base monomer in the monomer composition can be 59.9 mol % to 89.9 mol %, and may preferably be 75 mol % to 85 mol %.

A-1-1. Aromatic Ring-Containing Acrylate Monomer

The aromatic ring-containing acrylate monomer has an effect of improving the refractive index of the material for intraocular lens. The aromatic ring-containing acrylate monomer may have a phenoxy group, an alkylene group having two or less carbon atoms, and an acrylate bonding site. Specific examples of the aromatic ring-containing acrylate monomer include phenoxyethyl acrylate, phenylethyl acrylate, benzyl acrylate, phenyl acrylate, pentabromophenyl acrylate, and the like. The aromatic ring-containing acrylate monomer may be used alone or in combination of two or more, but from the viewpoint of copolymerizability or safety, it is desirable to use few types of the monomers, and preferably only one monomer is used alone.

From a point that an effect of improving the refractive index is great even when the aromatic ring-containing acrylate monomer is used alone, phenoxyethyl acrylate, phenylethyl acrylate and benzyl acrylate are preferred, and from a point of improving the flexibility, phenoxyethyl acrylate is particularly preferred.

A blending amount of the aromatic ring-containing acrylate monomer can be 25 mol % to 55 mol % when an amount of all the monomer components contained in the monomer composition is set as 100 mol %. From the viewpoint of exhibiting a high refractive index even in a water-absorbing state, the blending amount is preferably 30 mol % to 50 mol %, and more preferably 35 mol % to 45 mol %. If the blending amount of the aromatic ring-containing acrylate monomer is too high, there is a possibility that the flexibility and shape recovery property may be reduced due to a bulky structure of the aromatic ring-containing acrylate monomer. On the other hand, if the blending amount of the aromatic ring-containing acrylate monomer is too small, a desired refractive index may not be obtained.

A-1-2. Alkoxyalkyl Methacrylate Monomer

The alkoxyalkyl group of the alkoxyalkyl methacrylate monomer can be represented by the following chemical formula (1). The alkoxy group may be, for example, a methoxy group, an ethoxy group, and the like. The alkylene group to which the alkoxy group is bonded may be a methylene group, an ethylene group, and the like. The alkoxyalkyl methacrylate monomer is preferably methoxyethyl methacrylate and ethoxyethyl methacrylate, and more preferably ethoxyethyl methacrylate from the viewpoint of flexibility. The alkoxyalkyl methacrylate monomer can be used alone or used with two or more kinds mixed together.

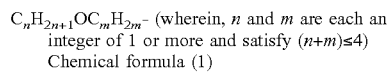

$C_nH_{2n+1}OC_mH_{2m}$- (wherein, $n$ and $m$ are each an integer of 1 or more and satisfy $(n+m) \leq 4$)

Chemical formula (1)

A blending amount of the alkoxyalkyl methacrylate monomer can be 1 mol % to 30 mol % when the amount of all the monomer components contained in the monomer composition is set as 100 mol %. From the viewpoint of suitably suppressing hydrolysis and the viewpoint of ease of folding, the blending amount is preferably 2 mol % to 25 mol % and more preferably 5 mol % to 20 mol %. In the base monomer, if the blending amount of the methacrylate monomer with respect to the acrylate monomer increases, problems such as glistening and the like tend to occur. The reason is not clear and is presumed to be that the acrylate monomer and the methacrylate monomer have different polymerization rates, and thus phase separation easily occurs (copolymerizability is poor), and glistening occurs easily as a result. On the other hand, in the present invention, by selecting the specific alkoxyalkyl methacrylate monomer described above, the ability to suppress glistening can be maintained even when the methacrylate monomer is used in the above blending amount.

A-1-3. Alkyl Acrylate Monomer

The alkyl acrylate monomer can contribute to further improvement in the shape recovery property and the flexibility of the material for intraocular lens. In addition, because the copolymerizability of the monomers can be improved, a higher ability to suppress glistening can be obtained.

The alkyl acrylate monomer may be, for example, a linear, branched or cyclic alkyl acrylate monomer and the like such as methyl acrylate, ethyl acrylate, propyl acrylate, butyl acrylate, pentyl acrylate, hexyl acrylate, heptyl acrylate, nonyl acrylate, stearyl acrylate, octyl acrylate, decyl acrylate, lauryl acrylate, pentadecyl acrylate, 2-ethylhexyl acrylate, cyclopentyl acrylate, cyclohexyl acrylate, and the like. In addition, a fluorine-substituted alkyl acrylate monomer such as 2,2,2-trifluoroethyl acrylate, 2,2,3,3-tetrafluoropropyl acrylate, 2,2,3,3-tetrafluoro-t-pentyl acrylate, 2,2,3,4,4, 4-hexafluorobutyl acrylate, 2,2,3,4,4,4-hexafluoro-t-hexyl acrylate, 2,3,4,5,5,5-hexafluoro-2,4-bis(trifluoromethyl) pentyl acrylate, 2,2,3,3,4,4-hexafluorobutyl acrylate, 2,2,2,2',2',2'-hexafluoroisopropyl acrylate, 2,2,3,3,4,4,4-heptafluorobutyl acrylate, 2,2,3,3,4,4,5,5-octafluoropentyl acrylate may also be included in the alkyl acrylate monomer. The alkyl acrylate monomer can be used alone or used with two or more kinds mixed together.

From the viewpoint of a great effect of improving the shape recovery property and the flexibility, an alkyl acrylate monomer having an alkyl group having 1 to 5 carbon atoms is preferred, ethyl acrylate and butyl acrylate are more preferred, and from the viewpoint of copolymerizability, ethyl acrylate is particularly preferred.

A blending amount of the alkyl acrylate monomer can be 0 mol % to 60 mol % when the amount of all the monomer components contained in the monomer composition is set as 100 mol %. The blending amount is preferably 15 mol % to 45 mol % and more preferably 20 mol % to 40 mol %.

A-2. Hydrophilic Monomer

The hydrophilic monomer can impart hydrophilicity to the material for intraocular lens. In addition, by adjusting the blending amount of the hydrophilic monomer, the flexibility and the strength can be maintained and occurrence of glistening can be suppressed. Although mechanism is not clear, it is presumed that the presence of a certain amount of the hydrophilic monomer in the material can prevent aggregation (glistening) of water in the polymer.

The hydrophilic monomer may be hydroxyl group-containing alkyl (meth)acrylate having an alkyl group having 1 to 20 carbon atoms, (meth)acrylamide and N-vinyllactam. The hydrophilic monomer can be used alone or used with two or more kinds mixed together. Moreover, in the specification, "(meth)acrylate" means acrylate and/or methacrylate.

The hydroxyl group-containing alkyl (meth)acrylate may be, for example, hydroxyalkyl (meth)acrylate such as hydroxyethyl (meth)acrylate, hydroxypropyl (meth)acrylate, hydroxybutyl (meth)acrylate, hydroxypentyl (meth)acrylate and the like, and dihydroxyalkyl (meth)acrylate such as dihydroxypropyl (meth)acrylate, dihydroxybutyl (meth)acrylate, dihydroxypentyl (meth)acrylate and the like.

The (meth)acrylamide may be, for example, N,N-dialkyl (meth)acrylamide such as N,N-dimethyl (meth)acrylamide, N,N-diethyl (meth)acrylamide, N,N-dipropyl (meth)acrylamide and the like, and N,N-dialkylaminoalkyl (meth)acrylamide such as N,N-dimethylaminopropyl (meth)acrylamide, N,N-diethylaminopropyl (meth)acrylamide and the like.

The N-vinyllactam may be, for example, N-vinyl pyrrolidone, N-vinyl piperidone, N-vinyl caprolactam and the like.

The hydrophilic monomer is not limited to the above monomers. Other usable hydrophilic monomers may be, for example, diethylene glycol mono(meth)acrylate, triethylene glycol mono(meth)acrylate, propylene glycol mono(meth) acrylate, (meth)acrylic acid, 1-methyl-3-methylene-2-pyrrolidinone, maleic anhydride, maleic acid, maleic acid derivatives, fumaric acid, fumaric acid derivatives, aminostyrene, hydroxystyrene, and the like.

From the point of a great effect of accelerating the reduction of glistening, the hydrophilic monomer is preferably hydroxyl group-containing alkyl (meth)acrylate and (meth)acrylamide and particularly preferably 2-hydroxyethyl methacrylate.

A blending amount of the hydrophilic monomer can be 10 mol % to 40 mol % when the amount of all the monomer components contained in the monomer composition is set as 100 mol %, and the blending amount is preferably 10 mol % to 25 mol %. In the range, the occurrence of glistening can be sufficiently suppressed and the flexibility can be maintained.

A-3. Cross-Linkable Monomer

The cross-linkable monomer may contribute to the flexibility of the material for intraocular lens. Specifically, good mechanical strength may be imparted and the shape recovery property may be improved. In addition, copolymerizability of the monomers may be improved.

The cross-linkable monomer may be, for example, butanediol di(meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl (meth)acrylate, trimethylolpropane tri (meth)acrylate, methacryloyloxyethyl (meth)acrylate, divinyl benzene, diallyl phthalate, diallyl adipate, triallyl diisocyanate, α-methylene-N-vinylpyrrolidone, 4-vinyl benzyl (meth)acrylate, 3-vinyl benzyl (meth)acrylate, 2,2-bis ((meth)acryloyloxyphenyl) hexafluoropropane, 2,2-bis ((meth)acryloyloxyphenyl) propane, 1,4-bis(2-(meth)acryloyloxyhexafluoroisopropyl) benzene, 1,3-bis(2-(meth) acryloyloxyhexafluoroisopropyl) benzene, 1,2-bis(2-(meth) acryloyloxyhexafluoroisopropyl) benzene, 1,4-bis(2-(meth) acryloyloxyisopropyl) benzene, 1,3-bis(2-(meth) acryloyloxyisopropyl) benzene, 1,2-bis(2-(meth) acryloyloxyisopropyl) benzene, and the like. In particular, one or more of butanediol di(meth)acrylate and ethylene glycol di(meth)acrylate may be preferably used. From a point of a great effect of controlling flexibility, impart good mechanical strength, and improving the shape recovery property and the copolymerizability, butanediol di(meth) acrylate is particularly preferred. The cross-linkable monomer can be used alone or used with two or more kinds mixed together.

A blending amount of the cross-linkable monomer can be 0.1 mol % to 5 mol % when the amount of all the monomercomponents contained in the monomer composition is set as 100 mol %. The blending amount is preferably 0.5 mol % to 4 mol % and more preferably 1 mol % to 3 mol %. In the range, the shape recovery property can be imparted, and the occurrence of glistening can be suppressed. In addition, an elongation rate that can withstand insertion from a small incision can be imparted to the material of intraocular lens.

A-4. Monomer Blending Ratio

A blending ratio on a molar basis (methacrylate/acrylate) of the total methacrylate monomer with respect to the total acrylate monomer in the monomer composition is 0.25 to 1.00, preferably 0.30 to 0.70, and more preferably 0.35 to 0.65. By setting the blending ratio of the acrylate monomer and the methacrylate monomer in the above range, the material of intraocular lens can be obtained in which the flexibility suitable for folding is maintained and the hydrolysis resistance is excellent.

A-5. Polymerization Initiator

The monomer composition contains a polymerization initiator as necessary. Any appropriate polymerization initiator such as a radical polymerization initiator, a photopolymerization initiator and the like may be used as the polymerization initiator depending on the polymerization method.

The radical polymerization initiator may be, for example, azobisisobutyronitrile, azobisdimethylvaleronitrile, benzoyl peroxide, t-butyl hydroperoxide, cumene hydroperoxide and the like. When the polymerization is carried out using light rays and the like, the photopolymerization initiator or a sensitizer is preferably added. The photopolymerization initiator may be, for example, a benzoin compound such as methyl orthobenzoyl benzoate and the like, a phenone compound such as 2-hydroxy-2-methyl-1-phenylpropane-1-one and the like, a thioxanthone compound such as 1-hydroxycyclohexyl phenyl ketone, 1-phenyl-1,2-propane-dione-2-(o-ethoxycarbonyl) oxime, 2-chlorothioxanthone and the like, dibenzosuberone, 2-ethylanthraquinone, benzophenone acrylate, benzophenone, benzyl, and the like.

A blending amount of the polymerization initiator or the sensitizer may be appropriately set within a range in which the effects of the present invention are not impaired.

A-6. Other Additive Components

The material for intraocular lens may contain other additive components such as an ultraviolet absorber, a dye and the like as necessary. Typically, the additive components can be blended into the material for intraocular lens by being added to the monomer composition.

The ultraviolet absorber may be, for example, benzophenones such as 2-hydroxy-4-methoxybenzophenone, 2-hydroxy-4-octoxybenzophenone and the like, benzotriazoles such as 2-(2'-hydroxy-5'-methacryloxyethyleneoxy-t-butylphenyl)-5-methyl-benzotriazole, 2-(2'-hydroxy-5'-methylphenyl) benzotriazole, 5-chloro-2-(3'-t-butyl-2'-hydroxy-5'-methylphenyl) benzotriazole and the like, salicylic acid derivatives, hydroxyacetophenone derivatives, and the like. A blending amount of the ultraviolet absorber can be set to any appropriate value as long as the effects of the present invention are not impaired.

When blue vision is corrected, the dye is desirably a yellow or orange dye for example. The dye may be, for example, a dye recited in Japanese Patent Laid-Open No. 2006-291006, an oil-soluble dye such as CI Solvent Yellow, CI Solvent Orange or a disperse dye such as CI Disperse Yellow, CI Disperse Orange, or a vat dye recited in Color Index (CI), and the like. A blending amount of the dye can be set to any appropriate value as long as the effects of the present invention are not impaired.

B. Method for Producing Material for Intraocular Lens

The material for intraocular lens is obtained by polymerizing the monomer composition. The polymerization method may be, for example, a method in which a radical polymerization initiator is blended and then heated, or a method in which electromagnetic waves such as microwaves, ultraviolet rays, and radiation rays (γ-rays) are irradiated. Heating conditions and irradiation conditions can be appropriately set according to the formulation of the monomer composition and the like.

The polymerization may be performed in a mold, and the material obtained after the polymerization may be processed into a desired shape by cutting.

C. Properties of Material of Intraocular Lens

In the material of intraocular lens of the present invention, the occurrence of glistening is suppressed. When the material of intraocular lens is processed into an intraocular lens, the number of occurrences of glistening is preferably 15 or less per intraocular lens. In addition, in a case of plates described in examples, the number of occurrences of glistening is preferably 6 or less per plate, and more preferably 2 or less.

The breaking stress of the material of intraocular lens is preferably 4.5 MPa to 11.0 MPa and more preferably 5.0 MPa to 10.5 MPa. If the breaking stress is less than 4.5 MPa, there is a possibility that the strength becomes weak, and the lens may be broken when the lens is inserted. In addition, the hydrolysis resistance may be insufficient. On the other hand, if the breaking stress exceeds 11.0 MPa, the flexibility may be reduced and the lens may be difficult to be folded into a small piece.

The elongation rate of the material of intraocular lens is preferably 170% or more. If the elongation rate is 170% or more, the material of intraocular lens is suitable for the insertion from small incision. In addition, from the viewpoint of the shape recovery property, the elongation rate is preferably 600% or less.

An elution rate of hydrolyzate (for example, phenoxyethyl alcohol (POEtOH)) from the material of intraocular lens when stored in water at 100° C. for 30 days is preferably 0.13 mass % or less and more preferably 0.10 mass % or less. In addition, the elution rate of hydrolyzate from the material of intraocular lens when stored in water at 100° C. for 60 days is preferably 0.80 mass % or less and more preferably 0.70 mass % or less. In addition, the elution rate of hydrolyzate from the material of intraocular lens when stored in water at 100° C. for 90 days is preferably 3.30 mass % or less and more preferably 2.80 mass % or less.

The refractive index of the material for intraocular lens is preferably 1.50 or more in both a dry state (25° C.) and a water-absorbing state (35° C.).

Preferably, the material for intraocular lens has a water absorption (mass %) in a range of 1.5 mass % to 4.5 mass %. When the water absorption is 1.5 mass % or more, the occurrence of glistening can be suppressed, and when the water absorption is 4.5 mass % or less, decrease in the flexibility and decrease in the shape recovery property can be further suppressed.

EXAMPLE

The present invention is specifically described below with reference to the examples, but the present invention is not limited to these examples. Moreover, each treatment and the measurement method of each property are as follows.

(Hydrolysis Treatment)

The sample is dried at 60° C. in advance, and a pre-treatment mass $W_0$ is measured. 50 mL of distilled water is put into a 100 mL pressure bottle, and the sample is immersed. The pressure bottle is put into a dryer at 100° C. and stored. 10 pieces of plates having a diameter of 6 mm and a thickness of 0.5 mm are used as samples. A tare weight $W_{01}$ of the bottle, a bottle mass $W_{02}$ after the addition to the distilled water, and a bottle mass $W_{03}$ after the sample immersion are recorded.

(POEtOH Elution Rate)

The following procedure is used to obtain the concentration and the elution rate of the phenoxyethyl alcohol (POEtOH, which is a hydrolyzate of POEA) for an extraction liquid 30 days after the hydrolysis treatment. After a bottle mass $W_{11}$ before collecting the extraction liquid is recorded, the extraction liquid is collected from the bottle, and a bottle mass $W_{12}$ after collecting the extraction liquid is recorded. The collected extraction liquid, a standard solution, and blanks (distilled water) of the collected extraction liquid and the standard solution are analysed using HPLC. After the analysis, the chromatogram of the distilled water is subtracted from the chromatogram of the collected aqueous solution and the chromatogram of the standard solution, which is to perform baseline correction. The peak area of POEtOH is calculated from the corrected chromatogram. A calibration curve is created from the concentration and the peak area of POEtOH of the standard solution. The concentration of POEtOH in the extraction liquid is calculated based on the peak area of the POEtOH of the extraction liquid and the obtained calibration curve. The elution rate of POEtOH in 1 g of the sample is calculated by the following equation (1) using the obtained concentration of POEtOH. The volume of the extraction liquid is calculated by an equation (2). In calculating the volume of the extraction liquid, there is a premise that change in mass of the sample out of the mass changed by heating at 100° C. is so small that the change can be neglected compared with that of the extraction liquid, and the density of the extraction liquid could be regarded as 1 g/1 mL because most of the extraction liquid is water. After the extraction liquid with the 30-day treatment is analysed, the bottle is put into the dryer at 100° C. again. After a total of 60 days of the hydrolysis treatment, an extraction liquid is collected again. As in the case of the 30-day treatment, a bottle mass $W_{21}$ before collecting the extraction liquid is recorded, the POEtOH concentration in the extraction liquid is quantified by HPLC analysis, and the elution rate of POEtOH is calculated by an equation (3). The volume of the extraction liquid is calculated by an equation (4). In addition, the elution rate of POEtOH after a total of 90 days of the hydrolysis treatment is also calculated similarly.

POEtOH elution rate (%)=POEtOH concentration in extraction liquid (ppm)×$10^{-6}$×extraction liquid volume $V_{1S}$ (mL)/pre-treatment mass $W_0$ (g)×100   Equation (1)

Extraction liquid volume $V_{1S}$ (mL≈g)=[$W_{02}$(g)−$W_{01}$(g)]−[$W_{03}$(g)−$W_{11}$(g)]   Equation (2)

POEtOH elution rate (%)=POEtOH concentration in extraction liquid (ppm)×$10^{-6}$×extraction liquid volume $V_{2S}$ (mL)/pre-treatment mass $W_0$(g)×100   Equation (3)

Extraction liquid volume $V_{2S}$ (mL≈g)=$V_{1S}$(mL≈g)−[$W_{11}$(g)−$W_{12}$(g)]−[$W_{12}$(g)−$W_{21}$(g)]   Equation (4)

(Breaking Stress)

The measurement is performed using a dumbbell-shaped test piece (see FIG. 1) having a total length (L0) of about 20 mm, a parallel part length (L) of 6 mm, a parallel part width (W) of 1.5 mm, and a thickness of 0.8 mm. The sample is immersed in constant temperature water of 25° C. and kept still for one minute, and then pulled at a speed of 100 mm/min until breaking. The breaking stress is obtained using software.

(Glistening)

In the measurement, a lens-shaped sample having a diameter of 6 mm and a central thickness of 0.8 mm±0.1 mm or a plate sample having a diameter of 6 mm and a thickness of 0.5 mm is used. For the lens-shaped sample, the sample is immersed in water of 35° C. for 17 hours or longer and then immersed in water of 25° C. for 2 hours, and thereafter, the appearance is observed with a stereoscopic microscope. For the plate sample, the sample is immersed in water of 35° C. for 22 hours and then immersed in water of 25° C. for 2 hours, and thereafter, the appearance is observed with a stereoscopic microscope. The observation of the appearance is performed on 2 or 3 test bodies for one kind of sample, and the number of glistening (bright spots) is examined. The magnification is about 10 to 60 times. The observation is performed with the magnification appropriately adjusted within the above range in a manner that the glistening could be easily observed.

(Water Absorption)

A mass of the sample in an equilibrium hydrated state at 25° C. and a dry state is measured, and the water absorption (mass %) is calculated. The water absorption is calculated by the following equation (5) using a mass Ww of the sample in the equilibrium hydrated state at 25° C. and a mass Wd of the sample in the dry state. Five plates having a diameter of 6 mm and a thickness of 0.8 mm are used as samples.

Water absorption (mass %)=(Ww−Wd)/Wd×100   Equation (5)

(Refractive Index)

A refractive index of a sample according to a Hg-e line is obtained using an Abbe refract meter. The measurement is performed on a dry sample (25° C.) or a water-absorbing sample (35° C.). A plate having a diameter 6 mm and a thickness 0.8 mm is used as the sample.

[Examples 1 to 6 and Comparative Examples 1 to 9 Preparation of Plate-Shaped Material for Intraocular Lens]

A monomer composition is obtained by adding a polymerization initiator to the monomer components with the ratios shown in Table 1., 0.5 part by mass of 2,2'-azobis(2, 4-dimethylvaleronitrile) is used as the specific substance of the polymerization initiator. The mass part of the polymerization initiator in the monomer composition is 0.5 part by mass with respect to 100 parts by mass of the base monomer. The obtained monomer composition is poured into a mold having a desired plate shape. The mold is put in an oven at 80° C. and subjected to heat polymerization molding for 40 minutes. The obtained polymer is released from the mold and subjected to an elution treatment, and then dried in an oven at 60° C. to obtain a plate-shaped material for intraocular lens. At this time, according to necessary measurement items, samples having two different thicknesses are appropriately prepared as plate samples having the same formulation. The 0.5 mm or 0.8 mm thick plate described above is a plate made from a mold in which a 0.5 mm or 0.8 mm thick spacer is used. According to the objective of the test, the dried plate is hollowed out to a diameter of 6 mm or 8 mm to make a plate for measurement.

TABLE 1

|  |  | Base monomer | | | Hydrophilic monomer | Cross-linkable monomer | Acrylate (A) | Methacrylate (MA) | |
| --- | --- | --- | --- | --- | --- | --- | --- | --- | --- |
|  |  | POEA Mol % | EA Mol % | ETMA Mol % | HEMA Mol % | BDDA Mol % | Mol % | Mol % | MA/A |
| Example | 1 | 40.3 | 25.8 | 16.3 | 14.9 | 2.6 | 68.8 | 31.2 | 0.45 |
|  | 2 | 38.7 | 24.7 | 15.7 | 19.0 | 1.9 | 65.3 | 34.7 | 0.53 |
|  | 3 | 38.9 | 24.9 | 15.8 | 19.2 | 1.3 | 65.1 | 34.9 | 0.54 |
|  | 4 | 36.7 | 23.5 | 14.9 | 22.6 | 2.4 | 62.6 | 37.4 | 0.60 |
|  | 5 | 36.9 | 23.6 | 15.0 | 22.7 | 1.8 | 62.3 | 37.7 | 0.60 |
|  | 6 | 37.1 | 23.8 | 15.0 | 22.9 | 1.2 | 62.1 | 37.9 | 0.61 |

TABLE 1-continued

|  |  | Base monomer | | | Hydrophilic monomer | Cross-linkable monomer | Acrylate monomer | Methacrylate monomer | |
|---|---|---|---|---|---|---|---|---|---|
|  |  | POEA Mol % | EA Mol % | ETMA Mol % | HEMA Mol % | BDDA Mol % | (A) Mol % | (MA) Mol % | MA/A |
| Comparative example | 1 | 36.8 | 47.2 |  | 13.6 | 2.4 | 86.4 | 13.6 | 0.16 |
|  | 2 | 37.1 | 47.4 |  | 13.7 | 1.8 | 86.3 | 13.7 | 0.16 |
|  | 3 | 35.7 | 45.6 |  | 17.6 | 1.2 | 82.4 | 17.6 | 0.21 |
|  | 4 | 44.9 |  | 36.4 | 16.6 | 2.2 | 47.1 | 52.9 | 1.12 |
|  | 5 | 42.2 |  | 34.2 | 20.8 | 2.7 | 45.0 | 55.0 | 1.22 |
|  | 6 | 42.5 |  | 34.5 | 20.9 | 2.1 | 44.6 | 55.4 | 1.24 |
|  | 7 | 40.2 |  | 32.5 | 24.7 | 2.6 | 42.8 | 57.2 | 1.34 |
|  | 8 | 40.4 |  | 32.7 | 24.9 | 2.0 | 42.4 | 57.6 | 1.36 |
|  | 9 | 40.7 |  | 33.0 | 25.0 | 1.3 | 42.0 | 58.0 | 1.38 |

[Components Used]
The abbreviations of the compounds described in the table are shown below.
<Base monomer>
POEA: 2-phenoxyethyl acrylate
EA: ethyl acrylate
POEMA: phenoxyethyl methacrylate
EHMA: ethylhexyl methacrylate
LMA: lauryl methacrylate
ETMA: ethoxyethyl methacrylate
<Hydrophilic monomer>
HEMA: 2-hydroxyethyl methacrylate
<Cross-linkable monomer>
BDDA: 1,4-butanediol diacrylate
Each property is evaluated for the obtained material for intraocular lens. Results are shown in Table 2.

As is clear from Tables 1 and 2, in Examples 1 to 6 and Comparative examples 4 to 9 in which the aromatic ring-containing acrylate monomer and the alkoxyalkyl methacrylate monomer having an alkoxyalkyl group having four or less carbon atoms are used in combination as the base monomer, materials of intraocular lens with improved hydrolysis resistance are obtained. In addition, in these materials of intraocular lens, occurrence of glistening is also suppressed. Furthermore, in Examples 1 to 6 in which the blending ratio on a molar basis of the methacrylate monomer with respect to the acrylate monomer in the monomer composition is within a range of 0.25 to 1.00, a material of intraocular lens is obtained which is flexible and can be suitably folded and which has a strength enough to withstand insertion into the eye. On the other hand, the materials of intraocular lens of Comparative examples 4 to 9 are

TABLE 2

|  |  | POEtOH elution 100° C. 30 days | | POEtOH elution 100° C. 60 days | | POEtOH elution 100° C. 90 days | | | Refractive index | | Breaking stress MPa | Water absorption % |
|---|---|---|---|---|---|---|---|---|---|---|---|---|
|  |  | ppm | Elution rate % | ppm | Elution rate % | ppm | Elution rate % | Glistening Spot[1] | 25° C. Dry | 35° C. Wet | | |
| Example | 1 | 3 | 0.10 | 15 | 0.43 | 49 | 1.31 | — | 1.525 | 1.519 | 5.6 | 1.8 |
|  | 2 | 3 | 0.09 | 12 | 0.37 | 38 | 1.06 | 0 | 1.524 | 1.518 | 6.1 | 2.2 |
|  | 3 | 3 | 0.08 | 13 | 0.33 | 41 | 0.97 | 1 | 1.524 | 1.518 | 6.5 | 2.5 |
|  | 4 | 3 | 0.09 | 13 | 0.36 | 37 | 0.95 | — | 1.524 | 1.517 | 8.3 | — |
|  | 5 | 2 | 0.07 | 10 | 0.29 | 29 | 0.79 | 1 | 1.524 | 1.517 | 9.3 | — |
|  | 6 | 3 | 0.09 | 13 | 0.34 | 36 | 0.88 | — | 1.524 | 1.517 | 9.7 | — |
| Comparative example | 1 | 6 | 0.18 | 40 | 1.24 | 192 | 5.57 | 2 | 1.523 | 1.517 | 3.9 | 1.7 |
|  | 2 | 6 | 0.19 | 43 | 1.28 | 205 | 5.80 | — | 1.523 | 1.517 | 3.4 | 1.6 |
|  | 3 | 6 | 0.17 | 38 | 1.03 | 176 | 4.47 | — | 1.522 | 1.516 | 4.4 | 2.2 |
|  | 4 | 2 | 0.06 | 5 | 0.16 | 10 | 0.27 | — | 1.527 | 1.521 | 11.7 | 2.0 |
|  | 5 | 2 | 0.06 | 6 | 0.17 | 10 | 0.28 | — | 1.527 | 1.521 | 11.8 | 2.4 |
|  | 6 | 2 | 0.06 | 6 | 0.18 | 10 | 0.29 | — | 1.527 | 1.520 | 11.3 | 2.7 |
|  | 7 | 2 | 0.06 | 6 | 0.18 | 10 | 0.27 | — | 1.526 | 1.520 | 15.6 | — |
|  | 8 | 2 | 0.05 | 5 | 0.16 | 8 | 0.23 | — | 1.526 | 1.520 | 17.7 | — |
|  | 9 | 2 | 0.06 | 6 | 0.17 | 11 | 0.29 | — | 1.526 | 1.519 | 16.7 | — |

[1]Measurement result using plates having a diameter of 6 mm and a thickness of 0.5 mm (average value of test number, n = 3).

expected to be low in flexibility and difficult to fold, or expected to have a large load when folded.

Comparative Examples 10 to 12 Preparation of Material for Intraocular Lens with a Lens Shape Except that the monomer components shown in Table 3 are used and the mold having the desired lens shape is used, a material for intraocular lens with a lens shape is obtained similarly to Example 1. In addition, glistening evaluation is performed on the obtained material for intraocular lens. Results are shown in Table 3.

TABLE 3

| | Base monomer | | | | | Hydrophilic monomer | Cross-linkable monomer | |
|---|---|---|---|---|---|---|---|---|
| | POEA Mol % | EA Mol % | POEMA Mol % | EHMA Mol % | LMA Mol % | HEMA Mol % | BDDA Mol % | Glistening (spot)[1] |
| Comparative example 10 | 43.0 | 27.5 | | | 10.8 | 15.9 | 2.8 | 19 |
| Comparative example 11 | 41.7 | 26.7 | | 13.5 | | 15.4 | 2.7 | 35 |
| Comparative example 12 | | 71.7 | 14.9 | | | 11.8 | 1.6 | ∞ |

[1]Measurement result with lenses (average value of test number, n = 2 or 3).

As shown in Table 3, when the aromatic ring-containing acrylate monomer and the alkoxyalkyl methacrylate monomer having an alkoxyalkyl group having four or less carbon atoms are not used in combination, the obtained material of intraocular lens is a material in which glistening occurs easily.

Test Examples 1 to 3

The polymer material which is obtained by polymerizing the monomer composition shown in Table 4 can also be suitably used as the material of intraocular lens of the present invention.

TABLE 4

| | | Base monomer | | | Hydrophilic monomer | Cross-linkable monomer | Acrylate monomer | Methacrylate monomer | |
|---|---|---|---|---|---|---|---|---|---|
| | | POEA Mol % | EA Mol % | ETMA Mol % | HEMA Mol % | BDDA Mol % | (A) Mol % | (MA) Mol % | MA/A |
| Test example | 1 | 37.0 | 35.5 | 7.5 | 18.2 | 1.8 | 74.3 | 25.7 | 0.35 |
| | 2 | 35.4 | 34.0 | 7.2 | 21.8 | 1.7 | 71.1 | 28.9 | 0.41 |
| | 3 | 35.6 | 34.2 | 7.2 | 21.9 | 1.2 | 70.9 | 29.1 | 0.41 |

INDUSTRIAL APPLICABILITY

The invention disclosed in the specification can be used for application relating to an intraocular lens.

What is claimed is:

1. A material for intraocular lens, comprising a polymer material which is obtained by polymerizing a monomer composition comprising a base monomer, a hydrophilic monomer which is a hydroxyl group-containing alkyl methacrylate having an alkyl group having 1 to 20 carbon atoms, and a cross-linkable monomer, wherein the base monomer comprises an aromatic ring-containing acrylate monomer, an alkoxyalkyl methacrylate monomer having an alkoxyalkyl group having four or less carbon atoms, and an alkyl acrylate monomer having an alkyl group having 1 to 20 carbon atoms, and the aromatic ring-containing acrylate monomer is one selected from phenoxyethyl acrylate, phenylethyl acrylate, and benzyl acrylate, the cross-linkable monomer is selected from butanediol diacrylate, ethylene glycol diacrylate, diethylene glycol diacrylate, triethylene glycol diacrylate, propylene glycol diacrylate, dipropylene glycol diacrylate, 2,2-bis(acryloyloxyphenyl) hexafluoropropane, 2,2-bis(acryloyloxyphenyl) propane, 1,4-bis(2-acryloyloxyhexafluoroisopropyl) benzene, 1,3-bis(2-acryloyloxyhexafluoroisopropyl) benzene, 1,2-bis(2-acryloyloxyhexafluoroisopropyl) benzene, 1,4-bis(2-acryloyloxyisopropyl) benzene, 1,3-bis(2-acryloyloxyisopropyl) benzene, and 1,2-bis(2-acryloyloxyisopropyl) benzene, a blending amount of the aromatic ring-containing acrylate monomer in the monomer composition is 30 mol % to 50 mol % when the amount of all the monomer components contained in the monomer composition is set as 100 mol %, a blending amount of the alkoxyalkyl methacrylate monomer in the monomer composition is 5 mol % to 25 mol % when the amount of all the monomer components contained in the monomer composition is set as 100 mol %, a blending amount of the alkyl acrylate monomer in the monomer composition is 20 mol % to 40 mol % when the amount of all the monomer components contained in the monomer composition is set as 100 mol %, and a blending ratio on a molar basis of the total methacrylate monomer with respect to the total acrylate monomer in all the monomer components contained in the monomer composition is 0.25 to 1.00.

2. The material for intraocular lens according to claim 1, wherein the alkoxyalkyl methacrylate monomer is one or more selected from methoxyethyl methacrylate and ethoxyethyl methacrylate.

3. The material for intraocular lens according to claim 1, wherein a blending amount of the hydrophilic monomer in the monomer composition is 10 mol % to 40 mol % when the amount of all the monomer components contained in the monomer composition is set as 100 mol %.

4. The material for intraocular lens according to claim 1, wherein a blending amount of the cross-linkable monomer in the monomer composition is 0.1 mol % to 5 mol % when the amount of all the monomer components contained in the monomer composition is set as 100 mol %.

5. The material for intraocular lens according to claim 1, wherein the breaking stress is 4.5 MPa to 11.0 MPa.

* * * * *